[19] United States Patent
Butland

[11] Patent Number: 4,882,195
[45] Date of Patent: Nov. 21, 1989

[54] METHOD FOR LABELING AN OBJECT FOR ITS VERIFICATION

[75] Inventor: Charles L. Butland, Marina Del Rey, Calif.

[73] Assignee: Print-Lock Corp., Playa Del Rey, Calif.

[21] Appl. No.: 868,955

[22] Filed: May 30, 1986

Related U.S. Application Data

[63] Continuation-in-part of Ser. No. 857,929, Apr. 30, 1986, abandoned.

[51] Int. Cl.$^4$ ............................ A61B 5/10; B41M 3/14
[52] U.S. Cl. ............................................ 427/1; 427/7; 427/145; 427/255.6
[58] Field of Search .................... 427/1, 7, 255.6, 145, 427/157

[56] References Cited

U.S. PATENT DOCUMENTS

| | | | |
|---|---|---|---|
| 1,374,208 | 4/1921 | Jones | 427/1 |
| 2,938,292 | 5/1960 | Jakowsky et al. | 427/1 |
| 3,694,240 | 9/1972 | Miller et al. | 427/1 |
| 4,176,205 | 11/1979 | Moling | 427/1 |
| 4,253,086 | 2/1981 | Szwarcbier | 340/146.3 E |
| 4,338,025 | 7/1982 | Engel | 356/71 |
| 4,504,408 | 3/1985 | Morton | 427/1 |
| 4,550,041 | 10/1985 | Thompson | 427/1 |

Primary Examiner—Janice A. Bell
Attorney, Agent, or Firm—Mueller and Smith

[57] ABSTRACT

Disclosed is a method for labeling an object for its identification. The method comprises applying a selected person's fingerprint to said object at a predetermined location upon said object. Next, the predetermined location is exposed to a vaporous agent comprising vapors of a cyanoacrylate ester. The selected person's fingerprint or said vapors of cyanoacrylate ester bear a detectable amount of an ultra-violet radiation sensitive dye. Exposing the predetermined location to said vapors create a permanent impression of the fingerprint on the object which impression is perceptible only in the presence of UV radiation. Prime objects for identification in accordance with the method of the present invention include works of art, negotiable instruments, credit card receipts, and like objects.

2 Claims, No Drawings

METHOD FOR LABELING AN OBJECT FOR ITS VERIFICATION

CROSS-REFERENCE TO RELATED APPLICATION

This application is a continuation-in-part of U.S. patent application Ser. No. 857,929 filed Apr. 30, 1986, entitled "Method for Labeling an Object for its Verification" now abandoned.

BACKGROUND OF THE INVENTION

The present invention relates to the labeling of objects for verifying authenticity and more particularly to the use of a selectedly-perceptible fingerprint therefor.

Many objects require verification for authenticity. Such objects include paintings, sculptures, and like works of art; video cassette recorders, televisions, and like household objects; computers, printers, and like office and business equipment; packages in which valuable objects are being transported; and the like. Works of art and like objects need to be authenticated and documented so that the owner knows that they are genuine. This same knowledge also is required by an insurance company prior to insuring a work of art. With respect to the authentication and documentation of works of art, for example, a detailed and exhaustive undertaking is required to be conducted by a recognized and bonded expert. This procedure includes physical authentication utilizing detection methods involving the use of infrared spectroscopy, X-ray radiography, ultra-violet spectroscopy, raking light procedures, pigment analysis, and like procedures. For a lithograph, for example, the lithograph must be unframed and free of obstacles for inspection. A careful scrutiny of the entire print, back and front surface, must be undertaken in order to detect evidence of variations from perfection including tears or folds, bacterial action, smudges, handprints, dirt, stains and like imperfections which originate both from the original printing and from later abrasion thereof. Observation additionally must extend to the kind of base material used, total count of colors and variations, and other variations from the normal. It will be observed that only a qualified expert can undertake such an examination.

Next, the historical information of the work of art must be considered. For a painting, for example, the history of the painting must be recorded and verified. This history includes where the painting came from, the date of origin of the painting, all sales records and auction records of the painting, diaries of the painting, and specific collector or museum documentation which accompanies the painting.

Now, such procedure for authentication of works of art ordinarily is required when the work of art is insured, when the art changes ownership, and even when the work of art is placed on loan and then returned. It will be observed that the recommended authentication procedure involves much time and expense. Nevertheless, museums, owners of works of art, insurance companies, and like interested parties must insist on such authentication procedures for their own protection.

Other instances of identification include the ability to verify ownership of more-common objects such as household appliances, business equipment, and like objects. Often, these objects have no serial number or other unique means of identification, or the identification number can be removed easily following a theft. Thus, a simple method for reliably identifying such objects would be welcomed by their owners.

Still another field which requires verification of ownership involves credit cards and checks, for example. Credit card theft amounts to millions of dollars annually, yet detection of the unauthorized use of a credit card often is difficult or inconvenient for the store owner. The same holds true for negotiable instruments like checks. Thus, there is a substantial need for providing either a deterent against those who would improperly and illegally utilize credit cards or stolen checks, or for the apprehension of such individuals following such unauthorized or illegal use.

BROAD STATEMENT OF THE INVENTION

The present invention is addressed to providing a simple, yet reliable method for labeling an object for its verification. The method of the present invention comprises applying a selected person's fingerprint to the object at a pre-determined location upon said object. Next, the predetermined location is exposed to a vaporous agent comprising vapors of a cyanoacrylate ester. Either the fingerprint or the cyanoacrylate ester bears a detectable amount of an agent. The vaporous agent creates a permanent impression of the fingerprint on the object, which impression is perceptible only in the presence of selected wavelengths of energy by virtue of said agent. Desirably, the agent is an ultra-violet radiation sensitive compound or dye which is not visually perceptible except upon application of ultraviolet (UV) radiation to the pre-determined location. Alternatively, the person's finger can contact a pad which bears a cyanoacrylate ester (optionally in a solvent) and UV dye and then the finger contacted at the pre-determined location on said object. A clear plastic laminate, for example, optionally can overlay the fingerprint location on the object.

Advantageously, the object can be a work of art, such as a painting or a sculpture. Alternatively, the object may be a credit card receipt or voucher utilized at the time that the credit card is used in making a purchase. At such point of purchase, the object also may be a negotiable instrument such as a check. In the latter two cases, the object is being identified, but more importantly, perhaps, so is the person utilizing the credit card or the check. Under such circumstances, the method of the present invention may become an effective deterent against the unauthorized use of credit cards and checks, which forms another aspect of the present invention.

Advantages of the present invention include a simple, yet reliable means for labeling objects for identification. Another advantage is that the label is not perceptible to people absent the application of appropriate wavelengths of energy such as UV radiation. Another advantage is that the label can last for an almost indefinite period of time. These and other advantages will become readily apparent to those skilled in the art based upon the disclosure contained herein.

DETAILED DESCRIPTION OF THE INVENTION

In the field of Dactyloscopy, latent fingerprints have been developed with cyanoacrylate esters as proposed in, for example, U.S. Pat. Nos. 3,523,628, 3,678,014, 4,103,081, 4,297,383, 4,407,842, and 4,461,235. In fact, a much improved cyanoacrylate ester aerosol spray method is disclosed in commonly-assigned application Ser. No. 849,380, filed Apr. 8, 1986. These prior proposals operate upon the apparent attraction of cyanoacrylate esters for amino acids and riboflavins secreted through the human skin and present in latent fingerprints. The result of the contact of vapors of cyanoacrylate with the latent fingerprint is a physical impression of the fingerprint that can be conventionally "lifted" by law enforcement personnel utilizing carbon dust, magnetic powder, talc, or the like techniques. Location of the fingerprints often is assisted by inclusion of a UV dye in the cyanoacrylate vapors which causes the developed latent fingerprints to fluoresce under the influence of UV radiation. Common in these prior proposals is the use of cyanoacrylate ester vapors for the detection of latent fingerprints so that the individual leaving the latent fingerprints can be identified. Most certainly this use of latent fingerprint detection is associated with crime and the apprehension of criminals.

The present invention is unique in its adaptation of cyanoacrylate development of latent fingerprints to uses far afield from the identification of criminals through the use of latent fingerprints. Indeed, the method of the present invention involves the application of such cyanoacrylate latent fingerprint technology to the labeling of objects for verifying their authenticity. Once an object is identified and verified, it can be labeled in accordance with the inventive technique disclosed herein so that its authentication at a later date is enhanced materially. Based upon the foregoing description in the field of art verification, it can be appreciated that art owners, insurance companies, and art experts can use all the assistance which can be provided for them in properly idetifying and verifying the authenticity of works of art. The present invention provides such assistance by providing a "invisible" label, the location of which on the object is not published and is not apparent to the naked eye. Only upon the application of selected wavelengths of energy at the right location on the object is the fingerprint label perceptible. Paintings and sculpures, for example, can be identified and authenticated initially with the authentication procedure involving the application of a fingerprint thereto. At a later date when the work of art needs to be authenticated again, not only can the owner utilize the services of an art expert in conjunction with the historical paperwork on the art, but the observance of the fingerprint label will provide further evidence as to the genuiness of the work of art being evaluated. That is, when a museum loans a work of art, it will know that the work of art being returned is the same work of art that was lent in the first instance.

By properly preserving the secrecy of the fingerprint labeling procedure, the value of the fingerprint label is enhanced. That is, the location of the fingerprint label can be controlled as well as whose fingerprint is applied thereto. In fact, combinations of fingerprints can be utilized at the same or at different locations on the object for providing further fool-proof means for labeling the object. Since Dactyloscopy is a recognized science by the courts, recognized experts for reading fingerprints can be utilized for verifying the authenticity of the fingerprint labels. As noted above, the fingerprint labeling technique of the present invention can be utilized on any object. Objects as common-place as television sets, video cassette recorders, and the like can be identified by the fingerprint label technique of the present invention. Should such objects be stolen, the criminal would not be able to mask the identity of the object by removing serial numbers applied by the manufacturer. Indeed, the fingerprint label could be located at almost any surface of the object so that its identity would be firmly established.

One useful technique for implementing the present invention involves the application of the fingerprint label to an object as described herein. Next, a fluorescent light would be shined upon the surface whereat the fingerprint is located and a record, e.g. photograph, of such surface and fingerprint label taken. The photograph would document the exact placement location of the fingerprint label. The photograph could be maintained within the files of the company offering such fingerprint labeling service. The likelihood of a fingerprint being placed in the same location is next to impossible, so that the fingerprint labeling technique of the present invention is a near-foolproof technique for labeling objects for their identification and verification.

Moreover, the present invention can be implemented to even a further degree of sophistication utilizing the new breed of "high tech" fingerprint computer equipment which currently is just being put into service by some law enforcement agencies. This aspect of the invention involves the maintenance of a duplicate copy of the fingerprint label applied to the object either on a card which the owner of the object retains or company offering such fingerprint labeling service retains. If the labeled object were stolen and recovered, or its authenticity questioned, the fingerprint could be identified. By cross-referencing the identified fingerprint, the object, e.g. a piece of art, actually could be identified and the true owner determined. This technique could be done through the use of a single fingerprint classification and identification system that currently exists within the law enforcement arena. Besides manual matching of fingerprints, the use of fingerprint computer equipment also could be implemented.

Another field which will benefit greatly by the fingerprint labeling technique of the present invention is the credit card and negotiable instrument field. Often, credit cards and checks (e.g. a negotiable instrument) are stolen and improperly used. At the point of sale, the sales clerk need only require the presenter of the credit card or check to place a fingerprint upon a surface of the credit card receipt or voucher, or upon the negotiable instrument itself, followed by exposure thereof to cyanoacrylate vapors, in order to be able to authenticate the credit card purchase or negotiable instrument being presented for payment. It is not likely that credit card or check thieves would be so ready to have their fingerprint permanently attached to the credit card receipt or check which leaves their possession and may eventually be presented to the police should the transaction be improper. Thus, the fingerprint labeling technique of the present invention should prove to be a deterent against the unauthorized use of credit cards and of stolen checks.

A further field which will benefit greatly by the fingerprint labeling technique of the present invention is the travel field, particularly with respect to the use of passports and visas by international travelers. The use of forged or false passports is an ever-increasing problem which customs officials at various international airports must deal with on a daily basis. Besides matching the physical description on the passport to the bearer thereof and the attempted verification of the genuineness of the passport, the fingerprint labeling technique of the present invention also could be utilized. Again, the passport would bear the non-removable and "invisible" fingerprint of the true bearer which could be accomplished at the issuance of the passport. Thereafter the fingerprint of the bearer could be matched to the fingerprint on the passport should questions as to the authenticity of the passport be raised upon its presentation. An advantage in using the fingerprint label of the present invention is the near-impossibility of removing the fingerprint from the face of the passport once it has been applied. While use of solvents or etching techniques may result in removal of the fingerprint, likely destruction of the surface of the passport would occur also. Such altercation, then would be detectable by the customs agent inspecting the passport. Thus, an effective technique for aiding customs officials in verifying the authenticity of passports is yet another advantage of the present invention.

As noted above, several prior proposals deal with the cyanoacrylate development of latent fingerprints. While any of those techniques can be used for implementation of the present invention, preferably, the cyanoacrylate ester aerosol spray method of Ser. No. 849,380 is utilized. The utilization of an aerosol container of cyanoacrylate ester has many advantages with respect to the application of the cyanoacrylate vapors to an object being fumed for the fixation of a fingerprint label. It may be desirable to include a UV dye in the cyanoacrylate ester itself as proposed in said co-pending application. Alternatively, for works of art, it may be prefered that the finger or thumb of the person whose print is being affixed to the object to be contacted with a pad or cloth containing the UV dye so that the latent fingerprint applied to the object, rather than the cyanoacrylate ester itself, contains the UV dye. The exposure of such a UV-impregnated fingerprint to vapors of cyanoacrylate ester still results in a fixed, permanent fingerprint which fluoresces in the presence of UV radiation. Also, this embodiment of the present invention does not expose sensitive areas of the object to air-borne UV dye which may damage the work of art itself. Alternativley, the person's finger can contact a pad which bears a cyanoacrylate ester (optionally in a solvent) and UV dye and then the finger contacted at the pre-determined location on said object. A clear plastic laminate, for example, optionally can overlay the fingerprint location on the object.

Alkyl esters of alpha-cyanoacrylates are known in the art. Typically, the alkyl ester group will be a $C_1$–$C_{18}$ group, advantageously a $C_1$–$C_6$ group, and preferably a $C_1$–$C_3$ alkyl group. In utilizing the preferred aerosol spray method, a halogenated organic solvent is included in the container which solvent is inert with respect to the cyanoacrylate, has a low boiling point (e.g. below about 167° F.) and desirably is non-flammable for safety purposes. Haloganated organic solvents which meet this diverse criteria include, for example, the low-boiling point chlorinated hydrocarbons or fluorocoarbons, chloro-flurocarbons, or mixtures thereof. These solvents additionally should not be deleterious to or damage the objects being exposed to the cyanoacrylate vapors. Preferred halogenated organic solvents are di-chloro fluoromethane, di-chloro tetra-fluoroethane, tri-chloroethane, tri-chloro fluoromethane, and the like and mixtures thereof. The cyanoacrylate ester spray method utilizes the mixture of cyanoacrylate and halogenated organic solvent which normally ranges from between about 1 and 99 percent by weight cyanoacrylate and advantageously this proportion is between about 1 and 10 percent by weight. The concentration of the mixture in the organic propellant often ranges from between about 50 to 60 percent by weight. The cyanoacrylate proportion, of course, can vary depending upon the type of cyanoacrylate, type of solvent, type of propellant, pressure of the contents in the container, oriface size, and like factors taught in the cited copending application. Preferred propellants are from the methane gas series and include, for example, ethane, propane, butane, pentane, and their halogenated derivatives, (e.g. mono-fluoroethane, mono-chloroethane, etc.) and the like and even mixtures thereof.

While the object to be fumed can be placed in a small room or like confined area for exposure to the cyanoacrylate ester vapors, preferably, a vapor tank specially constructed for such purpose is utilized. Such tanks have been proposed in the art. The preferred such tank is disclosed in commonly-assigned application Ser. No. 754,063, filed July 10, 1985. Such vapor tank, or a smaller or larger version thereof, advantageously can be utilized with the fingerprint labeling technique of the present invention. For credit card receipts and checks, for example, a smaller version which can be utilized at the point of sale in various stores is used to fume such small objects at the time the sale is made. The preferred vapor tank utilizes the preferred aerosol spray method which makes the fingerprint labeling operation extremely simple to utilize at the time that the sale is being made. In fact, only a matter of seconds or minutes are involved in the fixation of the applied fingerprint to the object. Should the person presenting the credit card or check refuse to have the fingerprint fixed, the sales clerk would be immediately alerted to the possibility of an unauthorized use taking place. The credit card or check can be confiscated immediately and appropriate security personnel notified.

Fluorescent dyes which may be utilized in the container bearing the cyanoacrylate ester or which may be contained in a gauze or pad impregnated therewith, include those fluorescent dyes conventionally proposed in the art in the latent fingerprint detection field. These fluorescent dyes include, for example, various rhodamines, such as Rhodamine B, or Hostacell yellow 8G (American Hoechst Corporation). The ultra-violet source exposes the fingerprint labels when shined on the object at the appropriate location where the fingerprint label is located.

It will be observed that the present invention has apparent utility in a wide variety of fields beyond those described herein. The disclosure herein illustrates the presently-known preferred embodiments for utilizing the fingerprint labeling technique of the present invention. It will be readily apparent to those skilled in the art that a wide variety of other objects may be suitably labeled in accordance with the precepts of the present invention for their identification. Such additional objects and circumstances are included within the scope of the present invention in accordance with the precepts thereof. All citations cited herein are incorporated expressly herein by reference.

I claim:

1. Method for labeling a work of art for its identification which comprises applying a selected person's fingerprint to said work of art at a predetermined location upon said work of art.

exposing said pre-determined location to a vaporous agent comprising vapors of a cyanoacrylate ester, said selected person's fingerprint or said vapors of cyanoacrylate ester bearing a detectable amount of an ultra-violet radiation sensitive dye, said exposing thereby creating a permanent impression of said fingerprint on said work of art which impression is perceptible only in the presence of UV radiation.

2. The method of claim 1 wherein said work of art is a painting.

* * * * *